United States Patent
Kadono et al.

[11] Patent Number: 6,132,725
[45] Date of Patent: Oct. 17, 2000

[54] REVERSE TRANSCRIPTASE INHIBITOR

[75] Inventors: Toshiko Kadono, Tokyo; Yoshihiro Sekino, Kanagawa; Sachio Wakayama, Tokyo, all of Japan

[73] Assignee: Masahito Hoashi, Tokyo, Japan

[21] Appl. No.: 09/167,543

[22] Filed: Oct. 7, 1998

[30] Foreign Application Priority Data

Oct. 23, 1997 [JP] Japan .................................. 9-290665

[51] Int. Cl.$^7$ ...................................... A61K 35/78
[52] U.S. Cl. ............................................. 424/195.1
[58] Field of Search .......................... 424/195.1

[56] References Cited

FOREIGN PATENT DOCUMENTS

| 0 694 306 A1 | 1/1996 | European Pat. Off. . |
|---|---|---|
| 934747 | 8/1999 | European Pat. Off. . |

*Primary Examiner*—Jon P. Weber
*Attorney, Agent, or Firm*—Nixon & Vanderhye

[57] ABSTRACT

A reverse transcriptase containing flowery portion or its extract originated from elm in *Ulmus hollandica* is disclosed. The reverse transcriptase of this invention shows an activity remarkably higher than that of a known reverse transcriptase inhibitor derived from *Ulmus davidiana* var. *japonica*. Low toxicity of the reverse transcriptase inhibitor of this invention allows it being successfully applied to pharmaceuticals with a potent activity at a low dose, foods and beverages.

9 Claims, No Drawings

REVERSE TRANSCRIPTASE INHIBITOR

This invention relates to a reverse transcriptase inhibitor originated from flowery portion of elm in *Ulmus hollandica*, and in more details to a reverse transcriptase inhibitor containing powder or extract of flowery portion of elm in *Ulmus hollandica*.

Recent global spreading of acquired immunodeficiency syndrome (AIDS) and human adult T cell Leukemia (HALT) urgently calls for authorized preventive and therapeutic methods.

It is well known that AIDS is developed by human immunodeficiency virus (HIV) and HALT is caused by human T cell leukemia virus. These viruses are referred to as retrovirus which is characterized by having reverse transcriptase capable of transcription from RNA to DNA.

Thus numbers of investigations have been directed to prevent the virus-caused development of AIDS by inhibiting activity of the reverse transcriptase contained in these retroviruses. These efforts have successfully resulted in development of various substances with reverse transcriptase inhibiting activities. Azidothymidine, dideoxycytidine, dideoxy-inosine, for example, having the reverse transcriptase inhibiting activitiesare approved as therapeutic remedies for AIDS. These therapeutic remedies are, however, disadvantageous in their high production costs and intense side effects.

To resolve these problems, it has been challenged to obtain components with reverse transcriptase inhibiting activities and less side effects, at low costs, from plants abundantly available in the nature. WO95/19782, for example, discloses preparation of reverse transcriptase inhibitor using flowery portion of *Ulmus davidiana* as a starting material.

The reverse transcriptase inhibitor thus obtained from the flowery portion of *Ulmus davidiana* is, however, not always satisfactory in its reverse transcriptase inhibiting activity although its safety is highly appreciated, which reserves yet room for improvement. The present inventors have thoroughly been investigating into providing a plant-originated reverse transcriptase inhibitor with a higher activity.

The present inventors have been searching various kinds of elm for their reverse transcriptase inhibiting activities and have incidentally found out an unexpectedly remarkable activity in the flowery portion of a specific kind of elm, which led to this invention. That is, this invention is to provide a reverse transcriptase inhibitor containing flowery portion of elm in *Ulmus hollandica* or its extract.

Plant species used as starting materials in this invention are not limited as far as they are included in *Ulmus hollandica*. *Ulmus hollandica* includes crossed varieties between *Ulmus carpinifolla* and *Ulmus glabra* and often gives a relatively large appearance. Surface of the twig is smooth and bare no fruit at the center of the wing in general. *Ulmus hollandica* is planted popularly on roadsides and in parks in Europe, whose garden variety also known.

Plant species included in *Ulmus hollandica* are exemplified as elm such as vegeta, commelin, groenveid, belgica, clusius, columella, dodoens and homestead.

Vegeta is a very stout elm having a plurality of main branches. The main branches of the young tree tend to extend obliquely but they will usually become spread laterally and somewhat downward as they grow. Thus the most branches are rambling and scattered in all directions. The trunk has a lot of long cleft and appears as gray. Leaf of vegeta is larger than that of belgica, described later, and is more flat than that of commelin. The leaf is widened in its base and shaped in a variety of forms such as reverse-ovoid or oval. The bud is usually large and appears as glossy and reddish brown. Huntingdon elm is also classified as vegeta.

Commelin is a stout elm with an opened crown. The trunk usually climbs up by some spiral but straight upward as a whole. The branch is more sparse and thinner than that of vegeta, and the color is typically reddish brown. The crown can often be seen through from the ground. The leaf is light green and small, and the vein looks bright in general. The leaves are sparsely arranged and fall significantly later than those of vegeta. The leaf is typically shaped in oval and has a short and sharp tip. Commelin is wind-proof in general and defoliates late in the season.

Groenveid is a large and wind-proof elm. It is approx. 15 to 20 meters in height and the tree top is divided into several sections to exhibit slim and well-featured crown in general. The leaves are small, very densely arranged, colored in dark green and completely turns yellow in autumn. Rear surface of the leaf is covered with down and appears in some dark color. Since the plant is a slow grower capable of bearing relatively a large amount of flowers and fruits, it is beneficial in terms of obtaining a larger quantity of flowery portion required in this invention from a single plant of elm.

Clusius is a wind-proof elm with a well-featured crown. Columella is a small-bodied elm. Dodoens is a stout elm with glossy dark green leaves and upwardly climbing boughs. Homestead is an elm mainly cultivated in the United States. Dodoens and Homestead have many resemblances to vegeta.

*Ulmus hollandica* used in this invention includes crossed varieties between *Ulmus carpinifolla* and *Ulmus glabra*.

*Ulmus carpinifolla* is approx. 25 to 30 meters in height and has a widened oval tree form. The wood texture becomes rougher with age. The twig is relatively thin and typically has no hair. The leaf is shaped in reverse-ovoid, has a length of less than 8 cm in general, and has approx. 12 pairs of veins extended toward right and left.

*Ulmus carpinifolla* includes a wide variety of elms such as dampieri, hoersholmiensis, sarniensis and wredei.

*Ulmus glabra* on the other hand is a large elm with a widened and round crown. The root is less developed. The bark, colored in gray, is smooth in its early days and is then shallowly grooved. Thick brown boughs are densely arranged and bark of the crown is colored in pink. The leaf is 8 to 16 cm long and the texture of which is often rougher than that of *Ulmus carpinifolla*. The petiole is generally short, entire part of which is overlapped with the slant leaf base. The veins extending toward right and left are composing 12 to 18 pairs. The inflorescence is rather large. The wing for flying the seed has a reverse-ovoid shape and bears the fruit in its center.

Elms included in *Ulmus glabra* are, for example, camperdownii, exoniensis and horizontalis.

It is allowable in this invention to use any plant species in *Ulmus hollandica* other than those mentioned above.

It is also allowable in this invention to use any plant species obtained by crossing a plant species in *Ulmus hollandica* with other plant species. Other plant species to be crossed with is either one in *Ulmus hollandica* or not in *Ulmus hollandica*. Either one or more kinds of species may be crossed. A crossed species may further be crossed. Thus a reverse transcriptase inhibitor of this invention includes all of those obtained from any plant species originated from *Ulmus hollandica*.

These plant species in *Ulmus hollandica* may be used separately or in combination with others in this invention.

This invention utilizes the flowery portion of plant species in *Ulmus hollandica* . The plant species in *Ulmus*

*hollandica* typically bears bud in the season from winter to spring and blooms in spring. The flower bud, even small in size, has reverse transcriptase inhibiting activity. It is thus desirable to collect the flowery portion within a period from its bud stage to the flower fall.

A potent reverse transcriptase inhibiting activity is detected in the flowery portion of the plant species in *Ulmus hollandica*, and this activity is significantly higher than that of *Ulmus davidiana* var. *japanica*. Of the plant species in *Ulmus hollandica*, especially remarkable reverse transcriptase inhibiting activity is observed in vegeta, commelin and groenveid. It has been unexpected at all that such a high activity is found exceptionally in plant species in *Ulmus hollandica* among a variety of elms.

The flowery portion of the plant species originated from *Ulmus hollandica* is utilized in any form convenient for use as a reverse transcriptase inhibitor. It is allowable, for example, to use a mixture of finely stripped or powdered flowery portion as mixed with appropriate components, or to use an extract obtained by extraction using a proper solvent.

Fine stripping or powdering of the flowery portion is enabled by processing the collected flowery portion using a cutter, a stripper or a colloidal mill and is more favorably done after the flowery portion is dried. The flowery portion is usually dried until the moisture content drops below 10 wt %, preferably below 5 wt % and still more preferably below 3 wt %. Either natural drying or mechanical drying is allowable. The drying is preferably started within 30 minutes after the collection of the flowery portion.

There is no special limitation on drying temperature. Thus drying by rapid heating is possible using a pressure drum heater or electromagnetic wave. Drying using the pressure drum heater is preferably done within a range from 80 to 140° C. A drying period is usually set within two minutes, more preferably within one minute, and still more preferably within 40 to 50 seconds. Electromagnetic wave-aided drying using a microwave oven is possible, for example, at 600 W for 20 to 50 seconds. Heating and drying under such conditions can suppress or inactivate undesirable activities of enzymes contained in the flowery raw material and can prevent to a certain extent components with the reverse transcriptase inhibiting activities from being degraded.

The flowery portion dried by the rapid heating may be used as it is or after dried further at low temperatures. The low temperature drying is preferably effected within a range from −5 to 10° C., which is effected by using a hot wind dryer such as an infrared dryer, ventilating heater or chilled dryer in a separate or combined manner. A possible case relates to, for example, infrared drying followed by chilled drying. Such low temperature drying can prevent active components for inhibiting reverse transcriptase from being decomposed.

The stripping or powdering of the flowery portion is effected using devices or tools selected by purposes. A colloidal mill, for example, can yield powder with a grain size of 50 to 100 μm. Such stripping or powdering is done before the drying, after the high temperature drying or after the low temperature drying.

Besides after being processed into such strip or powder, the flowery portion is possibly used also as an extract. The flowery portion to be extracted is any one of collected flowery portion itself, strip of the collected flowery portion, and those after being dried at high or low temperatures. It is preferable to make the flowery portion into strips to a certain fineness to raise extraction efficiency. Favorable solvents for the extraction include water and alcohols, whereas other extraction solvents also allowable. The alcoholic solvents are typically referred as to methanol, ethanol, propanol, isopropanol, butanol, isobutanol, tert-butanol, pentanol, isopentanol, hexanol and isohexanol. These solvents are used separately or in combination with the other. For example, a 30 to 50% ethanol aqueous solution or methanol aqueous solution is applicable.

The extraction is possibly proceeded at the room temperature or under reflux. An extraction device such as Soxhlet extractor is also available. A typical method relates to an extraction using a 50% ethanol aqueous solution under the reflux temperature in a Soxhlet extractor for 30 to 60 minutes.

Although obtained extract is available per se as a reverse transcriptase inhibitor, it is more preferable to use it after concentration aiming at a higher effect. Degree of the concentration differs according to use environments. Both of using a solution with a concentration of approx. 10% or removing the solvent until the extract becomes powder are allowable.

In this invention, it is possible to use only the above material obtained from plant species in *Ulmus hollandica* as a plant-originated component, or to use it in as combined with materials obtained from other plant species. Such materials obtained from other plant species are widely selectable from those having reverse transcriptase inhibiting activities.

In this invention, it is preferable to combine the above material in particular with leaf portion of varnish tree or its extract. Varnish trees to be used are chosen from Anacardiaceae. A most preferable source relates to leaf portion of plant species in Rhus of Anacardiaceae. Such species include *Rhus vernicitlua, Rhus trichocarpa, Rhus ambigna, Rhus javanica* and *Rhus sylvestris*. Soft young leaves are preferable as the leaf portion of these varnish trees. The leaves of eight-week-old or younger are more preferable, and those of four-week-old or younger are sill more preferable.

The leaf portion of these varnish trees are dried, powdered, stripped or extracted according to the above-mentioned processes similarly to those for the flowery portion of plant species of *Ulmus hollandica*. Mixing ratio of the flower-derived component of *Ulmus hollandica* and the leaf-derived component of varnish trees can be determined appropriately. It is generally set in a range of 1:0.1 to 10, and more preferably in a range of 1:0.5 to 2. A still more preferable ratio is approx. 1:2.

The reverse transcriptase inhibitor of this invention is applicable in a variety of styles by purposes. It is safely and effectively used as pharmaceuticals, foods and beverages.

For the case that a reverse transcriptase inhibitor of this invention is used as pharmaceuticals, various medicine forms are selectable according to the dosal route. The reverse transcriptase inhibitor of this invention is dosed both orally or parenterally, where typical doses include intrarectal dose, intranasal dose, buccal dose, hypoglossal dose, transvaginal dose, intramuscular dose, hypodermic dose and intravenous dose. Among which oral and hypodermic doses are most preferable.

Formulations suitable for the oral dose include tablet, capsule, powder, subtilized granule, granule, solution and syrup; and those suitable for the parenteral dose include injection, drop, suppository, inhalant, percutaneous absorbent, transmucosal adsorbent and cataplasm. The injection can be any one of those used in intravenous injection, intramuscular injection, hypodermic injection and drip. The reverse transcriptase inhibitor of this invention most preferably has a form of oral formulation, injection or cataplasm.

The reverse transcriptase inhibitor of this invention may be added with, as required, additives allowable in terms of pharmacology and medicine production. Possible additives include, for example, vehicle, disintegrator, disintegrator adjuvant, binder, lubricant, coating agent, dye, diluent, base, solubilizing agent or solubilizing adjuvant, isonicity, pH adjuster, stabilizer, propellant, adhesive, and moistening agent.

Proper combination of these additives can provide various additional functions to the reverse transcriptase inhibitor of this invention. It is possible, for example, to design the inhibitor so that the active component is released gradually as required. It is also possible to design the inhibitor so that the active component is released in a concentrated manner at internal body sites where the component is needed. Such controlled release formulation or drug delivery system is prepared according to processes generally known in the pharmaceutical industry.

Organic or inorganic carrier is applicable to the reverse transcriptase inhibitor of this invention. Such carrier includes lactose, starch, or oils and fats from plants or animals. An active component originated from *Ulmus hollandica* is available within a range of 0.01 to 100% to the reverse transcriptase inhibitor of this invention. The reverse transcriptase inhibitor of this invention is useful as a preventive or therapeutic remedy for AIDS and HALT.

The reverse transcriptase inhibitor of this invention can further be used as combined with other reverse transcriptase inhibitor. Combinations with, in particular, leaf portion of varnish trees are most preferable since synergistic effects are expectable. This invention thus includes a reverse transcriptase inhibition kit in which (1) flowery portion of *Ulmus hollandica* or its extract and (2) leaf portion of vanish trees or its extract are contained in any one of compositions constituting such kit.

It is acceptable that the components (1) and (2) are contained in any one of compositions comprising the reverse transcriptase inhibition kit. The kit may be, for instance, such that comprising a composition containing component (1) and a composition containing component (2), or that comprising a plurality of compositions individually containing components (1) and (2) at different ratios. At the time of their use, these compositions properly combined are dosed. It may be acceptable that a plurality of the compositions are dosed simultaneously or continuously, or dosed at given intervals if circumstances require.

Dose of the reverse transcriptase inhibitor of this invention is determined according to various conditions such as therapeutic or preventive purposes, sexuality, weight and age of patients, types and degrees of disease, medicine form, dosing route and number of times of dosing. Typical oral dose is effected with a dose of 0.1 $\mu$g to 100 mg (dry weight of active components) /kg weight/day and is given once a day or divided into several times, where the dose is not limited in the above range.

The reverse transcriptase inhibitor of this invention may be contained in various foods or beverages to provide functional foods or functional beverages. It may be added, for example, to black tea, refreshing drink, juice, candy, starchy foods and various processed foods. Amount of addition of the active component originated from *Ulmus hollandica* is selected within a range from 0.1 to 99%. It is also possible to use gelling agent or so as required to improve pleasantness to the palate.

This invention will be detailed hereinafter referring to the several preferred embodiments. Components, ratios and procedures shown in these embodiments can properly be altered without departing from the spirit of the invention. Thus the scope of the invention is not limited to the following embodiments.

EXAMPLE 1

An example of the reverse transcriptase inhibitor of this invention (powder) will be described.

Flower buds of vegeta, commelin and groenveid, all of which belong to *Ulmus hollandica,* were collected in March in Amsterdam City, the Netherlands. The collected flower buds were respectively crushed with a mixer and dried at 110 to 120° C. until the moisture contents were reduced to 1 to 5%. The obtained dried powders were sealed with a deoxidizing agent and stored at room temperature.

After being stored for one week, the dried powders were mixed with lactose and a 0.1% Blue No.1 aluminium lake lactose according to a ratio shown in the table below to prepare powders of this invention having reverse transcriptase inhibition activities.

TABLE 1

| Components | Weight part |
| --- | --- |
| Dried powder | 10 |
| 0.1% Blue No. 1 aluminium lake lactose | 0.01 |
| Lactose | 90 |

EXAMPLE 2

A typical example of a reverse transcriptase inhibitor (powder) of this invention as combined with a powder originated from young leaves of a varnish tree will be described.

Young leaves of a varnish tree were collected in March in Ishikawa Prefecture, Japan, crushed with a mixer, and dried at 110 to 120° C. until the moisture contents were reduced to 1 to 5%. The obtained dried powder was sealed with a deoxidizing agent and stored at room temperature. After one week of storage, it was added with the dried powders of vegeta, commelin and groenveid and starch and mixed. The dried powders and starch were mixed according to the quantities shown in the table below. Mixed powders of this invention having reverse transcriptase inhibition activities were thus prepared.

TABLE 2

| Components | Weight part |
| --- | --- |
| Dried powder of vegeta, commelin or groenveid | 5 |
| Dried powder of young varnish tree leaves | 10 |
| Starch | 85 |

EXAMPLE 3

A typical example of a reverse transcriptase inhibitor (capsule) of this invention will be described.

Individual powder formulations including powders of vegeta, commelin or groenveid prepared in Example 1 were filled in gelatin capsules to prepare capsule formulations having reverse transcriptase inhibiting activities.

Individual formulations including powders of vegeta, commelin, and groenveid as combined with the powder of varnish tree leaves prepared in Example 2 were filled in gelatin capsules to prepare capsule formulations having reverse transcriptase inhibiting activities.

EXAMPLE 4

A typical example of a reverse transcriptase inhibitor (injection) of this invention will be described.

Flower buds of vegeta, commelin and groenveid, all of which belong to *Ulmus hollandica* , were collected in March in Amsterdam, Netherlands. The collected flower buds were respectively crushed with a mixer and dried at 110 to 120° C. until the moisture contents were reduced to 1 to 5%. The obtained dried powders were sealed with a deoxidizing agent and stored at room temperature. After being stored for one week, individual dried powders were extracted with water at 80° C. and the solvent was then removed under reduced pressure. The obtained extracts were dissolved with sodium chloride into distilled water. The dried powders, sodium chloride and distilled water were mixed according to the quantities given in the table below. The resultant aqueous solutions were filtered to produce injections having reverse transcriptase inhibiting activities.

TABLE 3

| Components | Weight part |
| --- | --- |
| Extract | 0.5 |
| Sodium Chloride | 1.5 |
| Distilled water | 98.0 |

EXAMPLE 5

Typical examples of functional beverage will be described. Flower buds of vegeta, commelin and groenveid, all of which belong to *Ulmus hollandica*, were collected in March in Amsterdam, Netherlands. The collected flower buds were immediately stripped and then extracted with water at 60 ° C. The obtained extracts were concentrated to a solid content of 10% and then mixed with the components shown in the table below. A proportion of mixing the individual components followed the contents of the table. Functional beverages having reverse trascriptase inhibiting activities were thus prepared.

TABLE 4

| Components | Weight part |
| --- | --- |
| Extract | 5.0 |
| Fructose glucose liquid sugar | 11.0 |
| Citric acid | 0.2 |
| Sodium citrate | 0.1 |
| Apple juice | 3.0 |
| Apple flavor | 0.2 |
| Water | 80.5 |

TEST EXAMPLE 1

In this test example, compositions containing a variety of elms shown in Table 5 were compared in terms of reverse transcriptase inhibiting activity.

Using a reverse transcriptase derived from avian myeloblastosis virus, $IC_{50}$ (μg/ml)of the reverse transcriptase inhibitors prepared from each elm in Table 5 by the method mentioned in Example 4 were determined. The results were shown in Table 5 below.

TABLE 5

| Plant sources | $IC_{50}$ |
| --- | --- |
| *Ulmus hollandica* | |
| vegeta | 1 |
| commelin | 0.5 |
| groenveid | 1 |
| belgica | 3 |
| clusius | 5 |
| columella | 2 |

TABLE 5-continued

| Plant sources | $IC_{50}$ |
| --- | --- |
| dodoens | 3 |
| homestead | 3 |
| *Ulmus carpinifolla* | |
| dampieri | 25 |
| hoersholmiensis | 30 |
| *Ulmus glabra* | |
| camperdownii | 30 |
| exoniensis | 15 |
| other Ulms | |
| *Ulmus davidiana* var. japanica | 20 |
| *Ulmus americana* | 30 |
| *Ulmus pumila* | 25 |

Although flowery portions of a wide variety of elms other than those listed above were also measured for their reverse transcriptase inhibiting activities, none of them had a $IC_{50}$ value of 10 or below. The results indicated that compositions derived from flowery portion of elms in *Ulmus hollandica* have a remarkably high reverse transcriptase inhibiting activity. Of them, three species of vegeta, commelin and groenveid showed very potent activities. It has been also confirmed that mixing the flowery portion of species of *Ulmus hollandica* with young varnish tree leaves at a ratio by weight of 1:0.5 to 2 could intensify the reverse transcriptase inhibiting activity by approx. 2 to 5 times. A composition with a mixing ratio by weight of 1:2 had a markedly high activity. It should be noted that no toxicity was found in these assays for measuring reverse transcriptase inhibiting activity.

What is claimed is:

1. A reverse transcriptase inhibitor obtained from a strip or powdered flowery portion of *Ulmus hollandica* or an aqueous or lower alkanol extract thereof.

2. The reverse transcriptase inhibitor of claim 1 wherein said *Ulmus hollandica* is selected from the group consisting of vegeta, commelin, groenveid, belgica, clusius, columella, dodoens and homestead.

3. The reverse transcriptase inhibitor of claim 2 wherein said *Ulmus hollandica* is selected from the group consisting of vegeta, commelin and groenveid.

4. The reverse transcriptase inhibitor of claim 1 obtained from a dried powder of the flowery portion of *Ulmus hollandica*.

5. The reverse transcriptase inhibitor of claim 1 obtained by extracting the flowery portion of *Ulmus hollandica* at room temperature or by reflux with water or a lower alkanol.

6. The reverse transcriptase inhibitor of claim 1 additionally containing leaf portions from a varnish tree or an aqueous or lower alkanol extract thereof.

7. A food containing the reverse transcriptase inhibitor of claim 1.

8. A beverage containing the reverse transcriptase inhibitor of claim 1.

9. A reverse transcriptase inhibiting kit comprising (1) a reverse transcriptase inhibitor obtained from a flowery portion of *Ulmus hollandica*, or an aqueous or lower alkanol extract thereof, and (2) a reverse transcriptase inhibitor obtained from a leaf portion of a varnish tree or an aqueous or lower alkanol extract thereof.

* * * * *